(12) United States Patent
Himmelsbach et al.

(10) Patent No.: US 6,740,651 B2
(45) Date of Patent: *May 25, 2004

(54) AMINOQUINAZOLINES WHICH INHIBIT SIGNAL TRANSDUCTION MEDIATED BY TYROSINE KINASES

(75) Inventors: Frank Himmelsbach, Mittelbiberach (DE); Elke Langkopf, Warthausen (DE); Birgit Jung, Schwabenheim (DE); Stefan Blech, Warthausen (DE); Flavio Solca, Vienna (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/934,631

(22) Filed: Aug. 22, 2001

(65) Prior Publication Data

US 2002/0115675 A1 Aug. 22, 2002

Related U.S. Application Data

(60) Provisional application No. 60/230,542, filed on Sep. 5, 2000.

(30) Foreign Application Priority Data

Aug. 26, 2000 (DE) .......................................... 100 42 062

(51) Int. Cl.⁷ .................... C07D 413/12; C07D 498/04; A61K 31/5375; A61P 35/00
(52) U.S. Cl. ..................... 514/228.8; 544/119; 544/71; 514/234.5
(58) Field of Search ................ 544/119, 71; 514/234.5, 514/228.8

(56) References Cited

U.S. PATENT DOCUMENTS

| 5,760,041 A | 6/1998 | Wissner et al. |
| 6,002,008 A | 12/1999 | Wissner et al. |

FOREIGN PATENT DOCUMENTS

| EP | 0 787 722 A1 | 8/1997 |
| WO | WO 96 33980 A1 | 10/1996 |
| WO | WO 97 30035 A1 | 8/1997 |
| WO | WO 97 32856 A1 | 9/1997 |
| WO | WO 97 38983 A | 10/1997 |
| WO | WO 98 13354 A1 | 4/1998 |
| WO | WO 99 09016 A1 | 2/1999 |
| WO | WO 00 18740 A1 | 4/2000 |
| WO | WO 00 51991 A | 9/2000 |
| WO | WO 00 55141 A1 | 9/2000 |

OTHER PUBLICATIONS

Baselga et al. Why the epidermal growth factor receptor? the rationale for cancer therapy, The Ocologist7(suppl.4):2–8, 2002.*

Tsou et al; "6–Substituted–4–(3–bromophenylamino)quinazolines as Putative Irreversible Inhibitors of the Epidermal Growth Factor Receptor (EGFR)and Human Epidermal Growth Factor Receptor (HER–2) Tyrosine Kinases with Enhanced Antitumor Activity"; J. Med. Chem, 2001 ,44, 2719–2734.

Boschelli; "Small molecule inhibitors of receptor tyrosine kinases"; Review Article—Chemical Sciences.

* cited by examiner

Primary Examiner—Richard L. Raymond
Assistant Examiner—Hong Liu
(74) Attorney, Agent, or Firm—Robert P. Raymond; Alan R. Stempel; Mary-Ellen M. Devlin

(57) ABSTRACT

Compounds of the formula

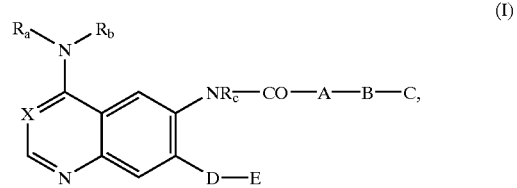

having an inhibitory effect on signal transduction mediated by tyrosine kinases, and the use thereof for treating diseases, particularly tumoral diseases, diseases of the lungs and respiratory tract.

8 Claims, No Drawings

AMINOQUINAZOLINES WHICH INHIBIT SIGNAL TRANSDUCTION MEDIATED BY TYROSINE KINASES

RELATED APPLICATIONS

Benefit of U.S. Provisional Application Serial No. 60/230,542, filed on Sep. 5, 2000 is hereby claimed.

DESCRIPTION OF THE INVENTION

The present invention relates to bicyclic heterocycles of general formula

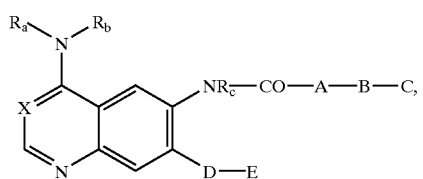

the tautomers, the stereoisomers and the salts thereof, particularly the physiologically acceptable salts thereof with inorganic or organic acids or bases which have valuable pharmacological properties, especially an inhibitory effect on signal transduction mediated by tyrosine kinases, the use thereof for treating diseases, particularly tumoral diseases, diseases of the lungs and respiratory tract, and the preparation thereof.

In the above general formula I $R_a$ denotes a hydrogen atom or a methyl group, $R_b$ denotes a phenyl, benzyl- or 1-phenylethyl group wherein the phenyl nucleus is substituted in each case by the groups $R_1$ to $R_3$, while $R_1$ and $R_2$, which may be identical or different, in each case denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group, a methyl or methoxy group substituted by 1 to 3 fluorine atoms or $R_1$ together with $R_2$, if they are bound to adjacent carbon atoms, denote a —CH=CH—CH=CH, —CH=CH—NH— or —CH=N—NH group and $R_3$ denotes a hydrogen, fluorine, chlorine or bromine atom, $R_c$ denotes a hydrogen atom or a methyl group, X denotes a methyne group substituted by a cyano group or a nitrogen atom, A denotes a 1,1- or 1,2-vinylene group which may be substituted in each case by one or two methyl groups or by a trifluoromethyl group, an ethynylene group or a 1,3-butadien-1,4-ylene group optionally substituted by a methyl or trifluoromethyl group, B denotes an alkylene or —CO-alkylene group wherein the alkylene moiety in each case contains 1 to 4 carbon atoms, while the linking of the —CO-alkylene group to the adjacent group A in each case must take place via the carbonyl group, a —CO—O-alkylene- or —CO—NR$_4$-alkylene group wherein the alkylene moiety in each case contains 1 to 4 carbon atoms, while the linking to the adjacent group A in each case must take place via the carbonyl group, wherein $R_4$ denotes a hydrogen atom or a methyl or ethyl group, or a carbonyl group, C denotes a 2-oxo-morpholin-4-yl group substituted by the group $R_5$ or by the group $R_5$ and a $C_{1-4}$-alkyl group, while $R_5$ denotes a $C_{3-4}$-alkyl, hydroxy-$C_{1-4}$-alkyl, $C_{1-4}$-alkoxy-$C_{1-4}$-alkyl, di-($C_{1-4}$-alkyl)-amino-$C_{1-4}$-alkyl, pyrrolidino-$C_{1-4}$-alkyl, piperidino-$C_{1-4}$-alkyl, morpholino-$C_{1-4}$-alkyl, 4-($C_{1-4}$-alkyl)-piperazino-$C_{1-4}$-alkyl, $C_{1-4}$-alkylsulphanyl-$C_{1-4}$-alkyl, $C_{1-4}$-alkylsulphinyl-$C_{1-4}$-alkyl, $C_{1-4}$-alkylsulphonyl-$C_{1-4}$-alkyl, cyano-$C_{1-4}$-alkyl, $C_{1-4}$-alkoxycarbonyl-$C_{1-4}$-alkyl, aminocarbonyl-$C_{1-4}$-alkyl, $C_{1-4}$-alkylaminocarbonyl-$C_{1-4}$-alkyl, di-($C_{1-4}$-alkyl)aminocarbonyl-$C_{1-4}$-alkyl, pyrrolidinocarbonyl-$C_{1-4}$-alkyl, piperidinocarbonyl-$C_{1-4}$-alkyl, morpholinocarbonyl-$C_{1-4}$-alkyl or a 4-($C_{1-4}$-alkyl)-piperazino-carbonyl-$C_{1-4}$-alkyl group, a 2-oxo-morpholin-4-yl group substituted by two groups $R_5$, where $R_5$ is as hereinbefore defined and the two groups $R_5$ may be identical or different, a 2-oxo-morpholin-4-yl group, wherein the two hydrogen atoms of a methylene group are replaced by a —(CH$_2$)$_m$—, —CH$_2$—Y—CH$_2$, —CH$_2$—Y—CH$_2$—CH$_2$, —CH$_2$CH$_2$—Y—CH$_2$CH$_2$— or —CH$_2$CH$_2$—Y—CH$_2$CH$_2$CH$_2$— bridge optionally substituted by one or two $C_{1-2}$-alkyl groups, while m denotes the number 2, 3, 4, 5 or 6 and Y denotes an oxygen or sulphur atom, a sulphinyl, sulphonyl or $C_{1-4}$-alkylimino group, a 2-oxo-morpholin-4-yl group, wherein a hydrogen atom in the 5 position together with a hydrogen atom in the 6 position is replaced by a —(CH$_2$)$_n$—, —CH$_2$—Y—CH$_2$, —CH$_2$—Y—CH$_2$CH$_2$— or —CH$_2$CH$_2$—Y—CH$_2$-bridge, while Y is as hereinbefore defined and n denotes the number 2, 3 or 4, or, if D together with E denotes a group $R_d$, it may also denote a 2-oxo-morpholin-4-yl group which may be substituted by 1 to 4 $C_{1-2}$-alkyl groups, D denotes a —O—$C_{1-6}$-alkylene group, while the alkylene moiety is linked to the group E, or an oxygen atom, while this may not be linked to a nitrogen atom of the group E, and E denotes an amino group substituted by 2 $C_{1-4}$-alkyl groups, wherein the alkyl groups may be identical or different and each alkyl moiety may be substituted from the 2 position by a $C_{1-4}$-alkoxy or di-($C_{1-4}$-alkyl)-amino group or by a 4- to 7-membered alkyleneimino group, while in the abovementioned 6- to 7-membered alkyleneimino groups in each case a methylene group may be replaced in the 4 position by an oxygen or sulphur atom or by a sulphinyl, sulphonyl- or N-($C_{1-4}$-alkyl)-imino group, a 4- to 7-membered alkyleneimino group optionally substituted by 1 to 4 methyl groups, a 6- to 7-membered alkyleneimino group optionally substituted by 1 or 2 methyl groups, wherein in each case a methylene group in the 4 position is replaced by an oxygen or sulphur atom or by a sulphinyl, sulphonyl- or N-($C_{1-4}$-alkyl)-imino group, an imidazolyl group optionally substituted by 1 to 3 methyl groups, a $C_{5-7}$-cycloalkyl group, wherein a methylene group is replaced by an oxygen or sulphur atom or by a sulphinyl, sulphonyl or N-($C_{1-4}$-alkyl)-imino group, or D together with E denotes a hydrogen atom, a $C_{1-6}$-alkoxy group optionally substituted from the 2 position by a hydroxy- or $C_{1-4}$-alkoxy group, a $C_{3-7}$-cycloalkoxy- or $C_{3-7}$-cycloalkyl-$C_{1-4}$-alkoxy group, or a group $R_d$, where $R_d$ denotes a $C_{2-6}$-alkoxy group which is substituted from the 2 position by a $C_{4-7}$-cycloalkoxy- or $C_{3-7}$-cycloalkyl-$C_{1-3}$-alkoxy group, a $C_{4-7}$-cycloalkoxy- or $C_{3-7}$-cycloalkyl-$C_{1-6}$-alkoxy group wherein the cycloalkyl moiety in each case is substituted by a $C_{1-4}$-alkyl, $C_{1-4}$-alkoxy, di-($C_{1-4}$-alkyl)-amino, pyrrolidino, piperidino, morpholino, piperazino, 4-($C_{1-2}$-alkyl)-piperazino, $C_{1-4}$-alkoxy-$C_{1-2}$-alkyl, di-($C_{1-4}$-alkyl)-amino-$C_{1-2}$-alkyl, pyrrolidino-$C_{1-2}$-alkyl, piperidino-$C_{1-2}$-alkyl, morpholino-$C_{1-2}$-alkyl, piperazino-$C_{1-2}$-alkyl- or 4-($C_{1-2}$-alkyl)-piperazino-$C_{1-2}$-alkyl group, while the abovementioned cycloalkyl moieties may additionally be substituted by a methyl or ethyl group, while, unless otherwise stated, by the aryl moieties mentioned in the definition of the abovementioned groups is meant a phenyl group which may be mono- or disubstituted by $R_6$, while the substituents may be identical or different and $R_6$ denotes a fluorine, chlorine, bromine or iodine atom, a $C_{1-2}$-alkyl, trifluoromethyl or $C_{1-2}$-alkoxy group, or two groups $R_6$, if they are bound to adjacent carbon atoms, together represent a $C_{3-4}$-alkylene, methylenedioxy or 1,3-butadien-1,4-ylene group.

Preferred compounds of the above general formula I are those wherein $R_a$ denotes a hydrogen atom, $R_b$ denotes a benzyl or 1-phenylethyl group or a phenyl group substituted by the groups $R_1$ and $R_2$, while $R_1$ denotes a hydrogen, fluorine, chlorine or bromine atom, a methyl, trifluoromethyl, cyano or ethynyl group and $R_2$ denotes a hydrogen or fluorine atom, $R_c$ denotes a hydrogen atom, X denotes a nitrogen atom, A denotes a 1,2-vinylene group, B denotes a $C_{1-4}$-alkylene group, C denotes a 2-oxo-morpholin-4-yl group substituted by the group $R_5$ or by the group $R_5$ and a $C_{1-4}$-alkyl group, while $R_5$ denotes a $C_{3-4}$-alkyl, $C_{1-2}$-alkoxy-$C_{1-4}$-alkyl, di-($C_{1-2}$-alkyl)-amino-$C_{1-4}$-alkyl, pyrrolidino-$C_{1-4}$-alkyl, piperidino-$C_{1-4}$-alkyl, morpholino-$C_{1-4}$-alkyl, 4-($C_{1-2}$-alkyl)-piperazino-$C_{1-4}$-alkyl, $C_{1-2}$-alkylsulphanyl-$C_{1-4}$-alkyl, $C_{1-2}$-alkylsulphinyl-$C_{1-4}$-alkyl, $C_{1-2}$-alkylsulphonyl-$C_{1-4}$-alkyl, cyano-$C_{1-4}$-alkyl, $C_{1-2}$-alkoxycarbonyl-$C_{1-4}$-alkyl, aminocarbonyl-$C_{1-4}$-alkyl, $C_{1-2}$-alkyl-aminocarbonyl-$C_{1-4}$-alkyl, di-($C_{1-2}$-alkyl)-aminocarbonyl-$C_{1-4}$-alkyl, pyrrolidinocarbonyl-$C_{1-4}$-alkyl, piperidinocarbonyl-$C_{1-4}$-alkyl, morpholinocarbonyl-$C_{1-4}$-alkyl- or a 4-($C_{1-2}$-alkyl)-piperazinocarbonyl-$C_{1-4}$-alkyl group, a 2-oxo-morpholin-4-yl group substituted by two groups $R_5$, while $R_5$ is as hereinbefore defined and the two groups $R_5$ may be identical or different, a 2-oxo-morpholin-4-yl group, wherein the two hydrogen atoms of a methylene group are replaced by a —$(CH_2)_m$—, —$CH_2$—Y—$CH_2$, —$CH_2$—Y—$CH_2$—$CH_2$— or —$CH_2CH_2$—Y—$CH_2CH_2$-bridge, while m denotes the number 2, 3, 4 or 5 and Y denotes an oxygen or sulphur atom, a sulphinyl, sulphonyl or $C_{1-2}$-alkylimino group, a 2-oxo-morpholin-4-yl group, wherein a hydrogen atom in the 5 position together with a hydrogen atom in the 6 position is replaced by a —$(CH_2)_n$, —$CH_2$—Y—$CH_2$, —$CH_2$—Y—$CH_2CH_2$— or —$CH_2CH_2$—Y—$CH_2$-bridge, where Y is as hereinbefore defined and n denotes the number 2, 3 or 4, or, if D together with E denotes a group $R_d$, it may also denote a 2-oxo-morpholin-4-yl group which may be substituted by 1 or 2 methyl or ethyl groups, D denotes a —O—$C_{1-4}$-alkylene group, while the alkylene moiety is linked to the group E, and E denotes a dimethylamino, diethylamino, pyrrolidino, piperidino, morpholino, 4-methyl-piperazino- or 4-ethyl-piperazino group or D together with E denotes a hydrogen atom, a methoxy, ethoxy, 2-methoxy-ethoxy, 3-methoxy-propyloxy, tetrahydrofuran-3-yloxy, tetrahydropyran-3-yloxy, tetrahydropyran-4-yloxy, tetrahydrofuranylmethoxy or tetrahydropyranylmethoxy group, a cyclobutyloxy, cyclopentyloxy, cyclohexyloxy, cyclopropylmethoxy, cyclobutylmethoxy, cyclopentylmethoxy or cyclohexylmethoxy group or a group $R_d$, where $R_d$ denotes a 2-(cyclobutyloxy)-ethoxy, 2-(cyclopentyloxy)-ethoxy, 2-(cyclopropylmethoxy)-ethoxy or 2-(cyclobutylmethoxy)-ethoxy group, the tautomers, stereoisomers and salts thereof.

Particularly preferred compounds of the above general formula I are those wherein $R_a$ denotes a hydrogen atom, $R_b$ denotes a 1-phenylethyl, 3-methylphenyl, 3-chlorophenyl, 3-bromophenyl- or 3-chloro-4-fluorophenyl group, $R_c$ denotes a hydrogen atom, X denotes a nitrogen atom, A denotes a 1,2-vinylene group, B denotes a methylene group, C denotes a 2-oxo-morpholin-4-yl group which is substituted by a methoxymethyl, methoxyethyl, ethoxymethyl, ethoxyethyl, dimethylaminomethyl, dimethylaminoethyl, diethylaminomethyl, diethylaminoethyl, cyanomethyl or cyanoethyl group, a 2-oxo-morpholin-4-yl group, wherein the two hydrogen atoms of a methylene group are replaced by a —$CH_2CH_2$—, —$CH_2CH_2CH_2$—, —$CH_2CH_2CH_2CH_2$—, —$CH_2CH_2CH_2CH_2CH_2$—, —$CH_2$—O—$CH_2CH_2$—, —$CH_2$—$NCH_3$—$CH_2CH_2$—, —$CH_2$—$NC_2H_5$—$CH_2CH_2$—, —$CH_2CH_2$—O—$CH_2CH_2$—, —$CH_2CH_2$—$NCH_3$—$CH_2CH_2$— or —$CH_2CH_2$—$NC_2H_5$—$CH_2CH_2$— bridge, a 2-oxo-morpholin-4-yl group, wherein a hydrogen atom in the 5 position together with a hydrogen atom in the 6 position is replaced by a —$CH_2CH_2CH_2$, —$CH_2CH_2CH_2CH_2$, —$CH_2$—O—$CH_2$, —$CH_2$—$NCH_3$—$CH_2$, —$CH_2$—$NC_2H_5$—$CH_2$, —$CH_2$—O—$CH_2CH_2$, —$CH_2$—$NCH_3$—$CH_2CH_2$, —$CH_2$—$NC_2H_5$—$CH_2CH_2$, —$CH_2CH_2$—O—$CH_2$, $CH_2CH_2$—$NCH_3$—$CH_2$— or —$CH_2CH_2$—$NC_2H_5$—$CH_2$— bridge, or, if D together with E denotes a group $R_d$, it may also denote a 2-oxo-morpholin-4-yl group which is substituted by 1 or 2 methyl groups, and D together with E denotes a hydrogen atom,
a methoxy, ethoxy, 2-methoxy-ethoxy, 3-methoxy-propyloxy, tetrahydrofuran-3-yloxy, tetrahydropyran-4-yloxy or tetrahydrofuranylmethoxy group,
a cyclobutyloxy, cyclopentyloxy, cyclopropylmethoxy, cyclobutylmethoxy or cyclopentylmethoxy group or
a group $R_d$, where
$R_d$ denotes a 2-(cyclobutyloxy)-ethoxy, 2-(cyclopentyloxy)-ethoxy, 2-(cyclopropylmethoxy)-ethoxy or 2-(cyclobutylmethoxy)-ethoxy group,
the tautomers, stereoisomers and salts thereof.

Most particularly preferred compounds of the above general formula I are those wherein
$R_a$ denotes a hydrogen atom,
$R_b$ denotes a 3-chloro-4-fluorophenyl group,
$R_c$ denotes a hydrogen atom,
X denotes a nitrogen atom,
A denotes a 1,2-vinylene group,
B denotes a methylene group,
C denotes a 2-oxo-morpholin-4-yl group which is substituted by a methoxymethyl or methoxyethyl group, or a 2-oxo-morpholin-4-yl group, wherein the two hydrogen atoms of a methylene group are replaced by a —CH$_2$CH$_2$—O—CH$_2$CH$_2$— bridge, and
D together with E denotes a hydrogen atom, a methoxy or cyclopropylmethoxy group,
the tautomers, stereoisomers and salts thereof.

The following particularly preferred compounds of the above general formula I are mentioned by way of example:
(1) 4-[(3-chloro-4-fluoro-phenyl)amino]-6- {[4-((R)-2-methoxymethyl-6-oxo-morpholin-4-yl)-1-oxo-2-buten-1-yl]amino}-7-cyclopropylmethoxy-quinazoline,
(2) 4-[(3-chloro-4-fluoro-phenyl)amino]-6- {[4-(2-oxo-1,9-dioxa-4-aza-spiro[5,5]undec-4-yl)-1-oxo-2-buten-1-yl]amino}-7-cyclopropylmethoxy-quinazoline and
(3) 4-[(3-chloro-4-fluoro-phenyl)amino]-6-({4-[2-(2-methoxy-ethyl)-6-oxo-morpholin-4-yl]-1-oxo-2-buten-1-yl}amino)-7-cyclopropylmethoxy-quinazoline,
the tautomers, stereoisomers and salts thereof.

The compounds of general formula I may be prepared, for example, by the following methods:
reacting a compound of general formula

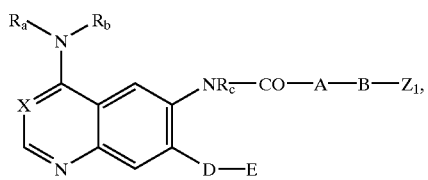

(II)

optionally formed in a reaction mixture, wherein
$R_a$ to $R_c$, A, B, D, E and X are as hereinbefore defined and
$Z_1$, denotes a leaving group such as a halogen atom, e.g. a chlorine or bromine atom, or a hydroxy group,
with a compound of general formula

H—C, (III)

wherein
C is as hereinbefore defined.

The reaction is optionally carried out in a solvent or mixture of solvents such as acetonitrile, methylene chloride, dimethylformamide, benzene, toluene, chlorobenzene, tetrahydrofuran, benzene/tetrahydrofuran or dioxane optionally in the presence of an inorganic or organic base and optionally in the presence of an activating agent, expediently at temperatures between −50 and 150° C., preferably at temperatures between −20 and 100° C.

With a compound of general formula II wherein $Z_1$, denotes a leaving group, the reaction is optionally carried out in a solvent or mixture of solvents such as methylene chloride, dimethylformamide, benzene, toluene, chlorobenzene, tetrahydrofuran, benzene/tetrahydrofuran or dioxane conveniently in the presence of a tertiary organic base such as triethylamine or N-ethyl-diisopropylamine, wherein these organic bases may simultaneously serve as solvent, or in the presence of an inorganic base such as sodium carbonate or potassium carbonate, expediently at temperatures between −50 and 150° C., preferably at temperatures between −20 and 100° C.

With a compound of general formula II wherein $Z_1$, denotes a hydroxy group, the reaction is preferably carried out in the presence of an activating agent, e.g. in the presence of thionyl chloride or phosphorus trichloride, conveniently in a solvent such as acetonitrile, methylene chloride, tetrahydrofuran, dioxane, toluene, chlorobenzene, ethylene glycol di-ethyl ether or sulpholane and optionally in the presence of a reaction accelerator such as sodium iodide at temperatures between −50 and 150° C., but preferably at temperatures between −20 and 100° C.

b) cyclising a compound of general formula

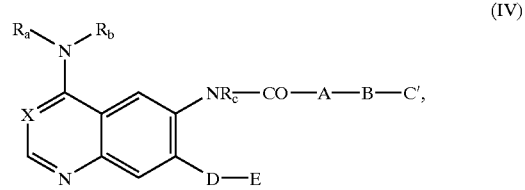

(IV)

optionally formed in a reaction mixture wherein
$R_a$ to $R_c$, A, B, D, E and X are as hereinbefore defined and
C' denotes a correspondingly substituted N-(carboxymethyl)-N-(2-hydroxyethyl)-amino or N-(C$_{1-4}$-alkyloxycarbonylmethyl)-N-(2-hydroxyethyl)-amino group which can be converted into a C group by cyclisation.

The reaction is optionally carried out in a solvent or mixture of solvents such as methylene chloride, acetonitrile, dimethylformamide, dimethylsulphoxide, sulpholane, benzene, toluene, chlorobenzene, tetrahydrofran, benzene/tetrahydrofuran or dioxane, expediently in the presence of an anhydrous acid such as trifluoroacetic acid, methanesulphonic acid or sulphuric acid or in the presence of a dehydrating agent, e.g. in the presence of isobutyl chloroformate, thionyl chloride, trimethylchlorosilane, phosphorus trichloride, phosphorus pentoxide, N,N'-dicyclohexyl carbodiimide, N,N'-dicyclohexyl carbodiimide/N-hydroxysuccinimide or 1-hydroxy-benzotriazole, N,N'-carbonyldiimidazole or triphenylphosphine/carbon tetrachloride, at temperatures between −20 and 200° C., but preferably at temperatures between −10 and 160° C.

In the reactions described hereinbefore, any reactive groups present such as hydroxy, carboxy or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, a protecting group for a carboxyl group may be a trimethylsilyl, methyl, ethyl, tert.butyl, benzyl or tetrahydropyranyl group and protecting groups for an imino group may be a formyl, acetyl, trifluoroacetyl, ethoxycarbonyl, tert.butoxycarbonyl, benzyloxycarbonyl, benzyl, methoxybenzyl or 2,4-diethoxybenzyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethylether.

A trifluoracetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

The compounds of general formulae II to IV used as starting materials are known from the literature in some cases or may be obtained by methods known from the literature (see Examples I to VII).

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible that the transmission of signals to components located further down is blocked.

The biological properties of the new compounds were investigated as follows:

The inhibition of EGF-R-mediated signal transmission can be demonstrated e.g. with cells which express human EGF-R and whose survival and proliferation depend on stimulation by EGF or TGF-alpha. A cell line of murine origin dependent on interleukin-3-(IL-3) which was genetically modified to express functional human EGF-R was used here. The proliferation of these cells known as F/L-HERc can therefore be stimulated either by murine IL-3 or by EGF (cf. von Rüden, T. et al. in EMBO J. 7, 2749–2756 (1988) and Pierce, J. H. et al. in Science 239, 628–631 (1988)).

The starting material used for the F/L-HERc cells was the cell line FDC-$P_1$, the production of which has been described by Dexter, T. M. et al. in J. Exp. Med. 152, 1036–1047 (1980). Alternatively, however, other growth-factor-dependent cells may also be used (cf. for example Pierce, J. H. et al. in Science 239, 628–631 (1988), Shibuya, H. et al. in Cell 70, 57–67 (1992) and Alexander, W. S. et al. in EMBO J. 10, 3683–3691 (1991)). For expressing the human EGF-R cDNA (cf. Ullrich, A. et al. in Nature 309, 418–425 (1984)) recombinant retroviruses were used as described by von Ruden, T. et al., EMBO J. 7, 2749–2756 (1988), except that the retroviral vector LXSN (cf. Miller, A. D. et al. in BioTechniques 7, 980–990 (1989)) was used for the expression of the EGF-R cDNA and the line GP+E86 (cf. Markowitz, D. et al. in J. Virol. 62, 1120–1124 (1988)) was used as the packaging cell.

The test was performed as follows:

F/L-HERc cells were cultivated in RPML/1640 medium (BioWhittaker), supplemented with 10% foetal calf serum (FCS, Boehringer Mannheim), 2 mM glutamine (BioWhittaker), standard antibiotics and 20 ng/ml of human EGF (Promega), at 37° C. and 5% $CO_2$. In order to investigate the inhibitory activity of the compounds according to the invention, $1.5 \times 10^4$ cells per well were cultivated in triplicate in 96-well dishes in the above medium (200 μl), the cell proliferation being stimulated with either EGF (20 ng/ml) or murine IL-3. The IL-3 used was obtained from culture supernatants of the cell line X63/0 mIL-3 (cf. Karasuyama, H. et al. in Eur. J. Immunol. 18, 97–104 (1988)). The compounds according to the invention were dissolved in 100% dimethylsulphoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer 96™ Aqueous Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom. The following results were obtained:

| Compound (Example No.) | Inhibition of the EGF-dependent proliferation $IC_{50}$ [nM] |
|---|---|
| 1 | 2 |

The compounds of general formula I according to the invention thus inhibit the signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation of tyrosine kinases, e.g. in inflammatory diseases of the airways such as chronic bronchitis, chronic obstructive bronchitis, asthma, bronchiectasias, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome, also for treating nasal polyps and polyps of the gastrointestinal tract of various origins, such as for example villous or adenomatous polyps of the large bowel, but also polyps in familial polyposis coli, intestinal polyps in Gardner's syndrome, polyps throughout the entire gastrointestinal tract in Peutz-Jeghers Syndrome, inflammatory pseudopolyps, juvenile polyps, colitis cystica profunda and pneumatosis cystoides intestinales.

Moreover, the compounds of general formula I and the physiologically acceptable salts thereof may be used to treat kidney diseases, particularly cystic changes as in cystic kidneys, for treating renal cysts which may be idiopathic in origin or which occur in syndromes such as e.g. tubercular sclerosis, in von-Hippel-Lindau Syndrome, in nephronophthisis and spongy kidney and other diseases caused by abnormal functioning of tyrosine kinases such as e.g. epidermal hyperproliferation (psoriasis), inflammatory processes, diseases of the immune system, hyperproliferation of haematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic, broncholytic and/or anti-inflammatory activity. For treating diseases in the region of the gastrointestinal tract, these compounds may also be administered on their own or in conjunction with substances having an effect on motility or secretion or with anti-inflammatory substances. These combinations may be administered either simultaneously or sequentially.

These compounds may be administered either on their own or in conjunction with other active substances by intravenous, subcutaneous, intramuscular, intrarectal, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:

Preparation of the starting products:

EXAMPLE I

4-[(3-chloro-4-fluoro-phenyl)amino]-6-[(4-{N-[(ethoxycarbonyl)methyl]-N-((R)-2-hydroxy-3-methoxy-propyl)-amino}-1-oxo-2-buten-1-yl)amino]-7-cyclopropylmethoxy-quinazoline 1.34 ml of oxalyl chloride are pipetted into 1.29 g of bromocrotonic acid in 30 ml of methylene chloride, then another 65 μl of N,N-dimethylformamide are added. The reaction mixture is stirred for about 45 minutes at ambient temperature until the development of gas has ceased, and then evaporated to dryness. The crude bromocrotonic acid chloride is taken up in 15 ml of methylene chloride and, while being cooled in an ice bath, added dropwise within five minutes to a solution of 2.00 g of 6-amino-4-[(3-chloro-4-fluoro-phenyl)amino]-7-cyclopropylmethoxy-quinazoline and 2.91 ml of diisopropylethylamine in 60 ml of tetrahydrofuran. The reaction mixture is stirred for 45 minutes while cooling with an ice bath, then stirred for two hours at ambient temperature. Then a solution of 1.80 g of ethyl ((R)-2-hydroxy-3-methoxy-propylamino)-acetate in 5 ml of tetrahydrofuran is added. The reaction mixture is heated to 60° C. for about 40 hours. To work it up, the reaction mixture is evaporated down. The flask residue is dissolved in 200 ml of ethyl acetate, washed with 5% citric acid solution and saturated sodium chloride solution and evaporated down to about 100 ml. The concentrate is chromatographed through a silica gel column using ethyl acetate/methanol (100:0 to 70:30) as eluant. The title compound is obtained, contaminated with some already cyclised product, as a brownish foam.

Yield: 1.10 g (32% of theory), $R_f$ value: 0.42 (silica gel, methylene chloride/methanol= 9:1)

Mass spectrum (ESI$^-$): m/z=614, 616 [M–H]$^-$

The following compound is obtained analogously to Example I:

(1) 4-[(3-chloro-4-fluoro-phenyl)amino]-6-[(4- {N-[(4-hydroxy-tetrahydropyran-4-yl)methyl]-N-[(ethoxycarbonyl)methyl]-amino}-1-oxo-2-buten-1-yl) amino]-7-cyclopropylmethoxy-quinazoline $R_f$ value: 0.40 (silica gel, methylene chloride/methanol=9:1) Mass spectrum (ESI$^-$): m/z=640, 642 [M–H]$^-$ (2) 4-[(3-chloro-4-fluoro-phenyl)amino]-6-[(4-{N-[(ethoxycarbonyl)methyl]-N-((S)-2-hydroxy-3-methoxy-propyl)-amino}-1-oxo-2-buten-1-yl)amino]-7-cyclopropylmethoxy-quinazoline $R_f$ value: 0.30 (silica gel, methylene chloride/methanol= 20:1)

Mass spectrum (ESI$^+$): m/z=616, 618 [M+H]$^+$

EXAMPLE II 6-amino-4-[(3-chloro-4-fluoro-phenyl)amino]-7-cyclopropyl-methoxy-quinazoline 36.02 g of 4-[(3-chloro-4-fluoro-phenyl)amino]-7-cyclopropylmethoxy-6-nitro-quinazoline are suspended in a mixture of 1080 ml of ethanol, 144 ml of glacial acetic acid and 360 ml of water and refluxed, whereupon the substance goes into solution. 20.70 g of iron powder are then cautiously added batchwise. After 30 minutes the reaction is complete and the reaction mixture is evaporated to dryness. The residue is taken up in 1200 ml of methylene chloride/methanol (9:1) and made alkaline with 33% ammonia solution. The iron slurry is suction filtered through a high-speed filter and washed with 500 ml of methylene chloride/methanol (9:1). The brown filtrate is filtered through a silica gel package, washed with a total of 2000 ml of methylene chloride/methanol (9:1) and evaporated down. The flask residue is suspended with 140 ml of diethylether, suction filtered and and dried in the air.

Yield: 29.70 g (89% of theory),

Melting point: 208° C.

Mass spectrum (ESI$^+$): m/z=359, 361 [M+H]$^+$

EXAMPLE III

4-[(3-chloro-4-fluoro-phenyl)amino]-7-cyclopropylmethoxy-6-nitro-quinazoline 29.36 g of cyclopropylmethanol are dissolved in 310 ml of N,N-dimethylformamide and cooled to about 10° C. in an ice bath. Then 41.58 g of potassium tert. butoxide are added batchwise, while the temperature should remain below 15° C. The reaction mixture is then stirred for another 30 minutes at 10° C., after which time 31.19 g of 4-[(3-chloro-4-fluoro-phenyl)amino]-7-fluoro-6-nitro-quinazoline are added batchwise, while again the temperature should not exceed 15° C. The deep red reaction mixture is stirred for another hour at 15° C. For working up, the mixture is poured onto 2.5 l of water and neutralised with 2N hydrochloric acid. The yellowish precipitate formed is suction filtered, washed with water and dried at 50° C. in a drying cupboard.

Yield: 36.02 g (100% of theory),

Melting point: 204° C.

Mass spectrum (ESI$^+$): m/z=389, 391 [M+H]$^+$

EXAMPLE IV

Ethyl ((R)-2-hydroxy-3-methoxy-propylamino)-acetate

The crude product solution of ethyl [N-benzyl-N-((R)-2-hydroxy-3-methoxy-prop-1-yl)-amino]-acetate in ethanol obtained in Example V is combined with another 20 ml of absolute ethanol and hydrogenated in the presence of 500 mg of palladium (10% on activated charcoal) as catalyst for about another four hours at ambient temperature until the calculated amount of hydrogen has been absorbed. For working up, the catalyst is filtered off and the filtrate is evaporated down in vacuo, leaving a colourless viscous oil.

Yield: 1.90 g (88% of theory), $R_f$ value: 0.48 (silica gel, methylene chloride/methanol=9:1)

Mass spectrum (ESI$^+$): m/z=192 [M+H]$^+$

The following compounds are obtained analogously to Example IV:

(1) (2-hydroxy-4-methoxy-butylamino)-acetic acid (The hydrogenation is carried out in a mixture of methanol/water=10:1.) $R_f$ value: 0.80 (Reversed phase ready-made TLC plate (E. Merck), acetonitrile/water/trifluoroacetic acid=50:50:1)
Mass spectrum (ESI$^-$): m/z=176 [M–H]$^-$ (2) ethyl ((S)-2-Hydroxy-3-methoxy-propylamino)-acetate Mass spectrum (EI): m/z=191 [M]$^+$

EXAMPLE V

Ethyl [N-benzyl-N-((R)-2-hydroxy-3-methoxy-propyl)-amino]-acetate

A mixture of 2.20 g of ethyl N-benzylamino-acetate and 1.00 g of(R)(–)-2-(methoxymethyl)-oxirane (Fluka) in 10 ml of absolute ethanol is left to stand over a weekend under an argon atmosphere. The crude product solution obtained is further reacted without any more purification.

$R_f$ value: 0.57 (silica gel, cyclohexane/ethyl acetate=1:1)

Mass spectrum (ESI$^+$): m/z=282 [M+H]$^+$

The following compounds are obtained analogously to Example V:

(1) [N-benzyl-N-(2-hydroxy-4-methoxy-butyl)-amino]-acetic acid (the reaction is carried out with N-benzylglycine in 1N sodium hydroxide solution.) $R_f$ value: 0.57 (Reversed phase ready-made TLC plate (E. Merck), acetonitrile/water/trifluoroacetic acid=50:50:1) Mass spectrum (ESI$^-$): m/z=266 [M–H]$^-$ (2) ethyl [N-benzyl-N-((S)-2-hydroxy-3-methoxy-propyl)-amino]-acetate $R_f$ value: 0.57 (silica gel, cyclohexane/ethyl acetate=1:1) Mass spectrum (ESI$^+$): m/z=282 [M+H]$^+$

EXAMPLE VI

Ethyl(4-hydroxy-tetrahydropyran-4-yl)methylamino]-acetate 5.30 g of glycine ethyl ester hydrochloride are dissolved in 10 ml of saturated potassium carbonate solution. Then 10 g of solid potassium carbonate are added while cooling with an ice bath. The mass formed is extracted thoroughly several times with diethylether. The combined ether extracts are dried over sodium sulphate and evaporated down. The glycine ethyl ester is dissolved together with 4.20 g 1,6-dioxa-spiro[2.5]octane in 20 ml of absolute ethanol and and heated to 90° C. for about six hours in a Roth bomb. After cooling to ambient temperature the reaction mixture is evaporated down. The yellowish oily crude product is further reacted without any more purification.

Mass spectrum (ESI$^+$): m/z=240 [M+Na]$^+$

EXAMPLE VII

Methyl (2-hydroxy-4-methoxy-butylamino)-acetate hydrochloride 11.94 ml of thionylchloride are added dropwise, within 20 minutes, to a suspension of 5.80 g of (2-hydroxy-4-methoxy-butylamino)-acetic acid in 200 ml methanol while cooling with an ice bath. The reaction mixture is allowed to come up to ambient temperature overnight. For working up, the cloudy solution is evaporated to dryness. The residue is stirred several times with 100 ml aliquots of methanol, which is then distilled off in vacuo using the rotary evaporator. The viscous crude product is reacted further without any additional purification.

Yield: 8.70 g,

Mass spectrum (ESI$^+$): m/z=192 [M+H]$^+$

Preparation of the Final Compounds:

Example 1

4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 950 mg of 4-[(3-chloro-4-fluoro-phenyl)amino]-6-[(4-{N-[(ethoxycarbonyl)methyl]-N-((R)-2-hydroxy-3-methoxy-propyl)-amino}-1-oxo-2-buten-1-yl)amino]-7-cyclopropylmethoxy-quinazoline and 195 µl of methanesulphonic acid in 10 ml acetonitrile are refluxed for about four hours. For working up, the reaction mixture is cooled in a bath of ice water, mixed with 75 ml of ethyl acetate and 25 ml of saturated sodium hydrogen carbonate solution and vigorously stirred for 10 minutes. The organic phase is separated off, washed with saturated sodium hydrogen carbonate solution and saturated sodium chloride solution and dried over magnesium sulphate. The solvent is distilled off in vacuo, leaving a brownish foam.

Yield: 610 mg (69% of theory),

R$_f$ value: 0.55 (silica gel, methylene chloride/methanol=9:1)

Mass spectrum (ESI$^+$): m/z=570, 572 [M+H]$^+$

The following compounds are obtained analogously to Example 1:

(1) 4-[(3-chloro-4-fluoro-phenyl)amino]-6-{[4-(2-oxo-1,9-dioxa-4-aza-spiro[5,5]undec-4-yl)-1-oxo-2-buten-1-yl]amino}-7-cyclopropylmethoxy-quinazoline R$_f$ value: 0.53 (silica gel, methylene chloride/methanol=15:1) Mass spectrum (ESI$^-$): m/z=594, 596 [M-H]$^-$ (2) 4-[(3-chloro-4-fluoro-phenyl)amino]-6-{[4-((S)-2-methoxymethyl-6-oxo-morpholin-4-yl)-1-oxo-2-buten-1-yl]amino}-7-cyclopropylmethoxy-quinazoline R$_f$ value: 0.53 (silica gel, methylene chloride/methanol=9:1) Mass spectrum (ESI$^-$): $^{m/z=}$568, 570 [M-H]$^-$ Example 2

4-[(3-chloro-4-fluoro-phenyl)amino]-6-({4-[2-(2-methoxy-ethyl)-6-oxo-morpholin-4-yl]-1-oxo-2-buten-1-yl}amino)-7-cyclopropylmethoxy-quinazoline 1.68 ml of oxalyl chloride are pipetted into 1.61 g of bromocrotonic acid in 50 ml methylene chloride, then one more drop of N,N-dimethylformamide is added. The reaction mixture is stirred for about one hour at ambient temperature until the development of gas has ceased, and then evaporated to dryness. The crude bromocrotonic acid chloride is taken up in 20 ml of methylene chloride and while cooling with an ice bath added dropwise, within five minutes, to a solution of 2.50 g of 6-amino-4-[(3-chloro-4-fluoro-phenyl)amino]-7-cyclopropyl-methoxy-quinazoline and 12.14 ml of diisopropylethylamine in 75 ml of tetrahydrofuran. The reaction mixture is stirred for one hour while cooling with an ice bath, then for another two hours at ambient temperature. A solution of 8.20 g of methyl (2-hydroxy-4-methoxy-butylamino)-acetate hydrochloride in 15 ml N,N-dimethylformamide is added in one go. The reaction mixture is stirred for 24 hours at 75° C. For working up, the reaction mixture is evaporated to dryness and the flask residue is partitioned between 250 ml of ethyl acetate and 200 ml of 5% citric acid solution. The organic phase is washed with saturated sodium chloride solution, dried over magnesium sulphate and evaporated down. The crude product is purified by chromatography through a silica gel column using ethyl acetate as eluant. The cyclised product is obtained as a beige solid.

Yield: 825 mg (20% of theory),

R$_f$ value: 0.38 (silica gel, ethyl acetate)

Mass spectrum (ESI$^-$): m/z=582, 584 [M-H]–

The following compounds may be prepared analogously to the foregoing Examples and other methods known from the literature:

(1) 4-[(3-chloro-4-fluoro-phenyl)amino]-6-{[4-((S)-2-methoxymethyl-6-oxo-morpholin-4-yl)-1-oxo-2-buten-1-yl]amino}-7-methoxy-quinazoline (2) 4-[(3-chloro-4-fluoro-phenyl)amino]-6-{[4-((S)-2-methoxymethyl-6-oxo-morpholin-4-yl)-1-oxo-2-buten-1-yl]amino}-quinazoline (3) 4-[(R)-(1-phenyl-ethyl)amino]-6-({4-[2-(2-methoxy-ethyl)-6-oxo-morpholin-4yl]-1-oxo-2-buten-1-yl}amino)-quinazoline (4) 4-[(3-chloro-4-fluoro-phenyl)amino]-6-({4-[3-(2-methoxy-ethyl)-2-oxo-morpholin-4-yl]-1-oxo-2-buten-1-yl}amino)-7-cyclopropylmethoxy-quinazoline (5) 4-[(R)-(1-phenyl-ethyl)amino]-6-{[4-(2-oxo-1,9-dioxa-4-aza-spiro[5.5]undec-4-yl)-1-oxo-2-buten-1-yl]amino}-7-methoxy-quinazoline (6) 4-[(3-chloro-4-fluoro-phenyl)amino]-6-{[4-(2-oxo-perhydro-cyclopenta[1,4]oxazin-4-yl)-1-oxo-2-buten-1-yl]amino}-7-methoxy-quinazoline (7) 4-[(3-chloro-4-fluoro-phenyl)amino]-6-{[4-(5-oxo-perhydro-2,4-dioxa-7-aza-inden-7-yl)-1-oxo-2-buten-1-yl]amino}-7-methoxy-quinazoline Example 3

Coated tablets containing 75 mg of active substance

| 1 tablet core contains: | |
| --- | --- |
| active substance | 75.0 mg |
| calcium phosphate | 93.0 mg |
| corn starch | 35.5 mg |
| polyvinylpyrrolidone | 10.0 mg |

-continued

| 1 tablet core contains: | |
|---|---|
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate.

Blanks 13 mm in diameter are produced in a tablet-making machine and these are then rubbed through a screen with a mesh size of 1.5 mm using a suitable apparatus and mixed with the rest of the magnesium stearate. This granulate is compressed in a tablet-making machine to form tablets of the desired shape.

| Weight of core: | 230 mg |
|---|---|
| die: | 9 mm, convex |

The tablet cores thus produced are coated with a film consisting essentially of hydroxypropylmethylcellulose. The finished film-coated tablets are polished with beeswax.

Weight of coated tablet: 245 mg.

Example 4

Tablets containing 100 mg of active substance

| Composition: | |
|---|---|
| 1 tablet contains: | |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
|---|---|
| Diameter: | 10 mm, biplanar, facetted on both sides and notched on one side. |

Example 5

Tablets containing 150 mg of active substance

| Composition: | |
|---|---|
| 1 tablet contains: | |
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
|---|---|
| die: | 10 mm, flat |

Example 6

Hard gelatine capsules containing 150 mg of active substance

| 1 capsule contains: | |
|---|---|
| active substance | 50.0 mg |
| corn starch (dried) approx. | 80.0 mg |
| lactose (powdered) approx. | 87.0 mg |
| magnesium stearate | 3.0 mg |
| approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

Example 7

Suppositories containing 150 mg of active substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example 8

Suspension containing 50 mg of active substance

| 100 ml of suspension contain: | |
|---|---|
| active substance | 1.00 g |
| carboxymethylcellulose-Na-Salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:

The distilled water is heated to 70° C. The methyl and propyl p-hydroxybenzoates together with the glycerol and carboxy-methylcellulose sodium salt are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example 9

Ampoules containing 10 mg active substance

| Composition: | |
|---|---|
| active substance | 10.0 mg |
| 0.01 N hydrochloric acid q.s. | |
| double-distilled water ad | 2.0 ml |

Preparation:

The active substance is dissolved in the necessary amount of 0.01 N HCl, made isotonic with common salt, filtered sterile and transferred into 2 ml ampoules.

Example 10

Ampoules containing 50 mg of active substance

| Composition: | |
|---|---|
| active substance | 50.0 mg |
| 0.01 N hydrochloric acid q.s. | |
| double-distilled water ad | 10.0 ml |

Preparation:

The active substance is dissolved in the necessary amount of 0.01 N HCl, made isotonic with common salt, filtered sterile and transferred into 10 ml ampoules.

Example 11

Capsules for powder inhalation containing 5 mg of active substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

| weight of capsule: | 70.0 mg |
|---|---|
| size of capsule = | 3 |

Example 12

Solution for inhalation for hand-held nebulisers containing 2.5 mg active substance

| 1 spray contains: | |
|---|---|
| active substance | 2.500 mg |
| benzalkonium chloride | 0.001 mg |
| 1 N hydrochloric acid q.s. | |
| ethanol/water (50/50) ad | 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges). Contents of the container: 4.5 g

What is claimed is:

1. A compound of the formula

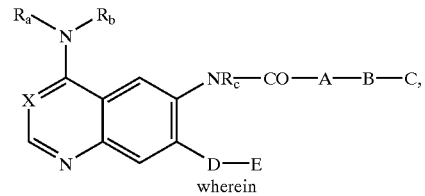

wherein $R_a$ denotes a hydrogen atom or a methyl group, $R_b$ denotes a phenyl, benzyl- or 1-phenylethyl group wherein the phenyl nucleus is substituted in each case by the groups $R_1$ to $R_3$, while $R_1$ and $R_2$, which may be identical or different, in each case denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group, a methyl or methoxy group substituted by 1 to 3 fluorine atoms or $R_1$ together with $R_2$, if they are bound to adjacent carbon atoms, denote a —CH=CH—CH=CH, —CH=CH—NH— or —CH=N—NH group and $R_3$ denotes a hydrogen, fluorine, chlorine or bromine atom, $R_c$ denotes a hydrogen atom or a methyl group, X denotes a nitrogen atom, A denotes a 1,1- or 1,2-vinylene group which may be substituted in each case by one or two methyl groups or by a trifluoromethyl group, an ethynylene group or a 1,3-butadien-1,4-ylene group optionally substituted by a methyl or trifluoromethyl group, B denotes an alkylene or —CO-alkylene group wherein the alkylene moiety in each case contains 1 to 4 carbon atoms, while the linking of the —CO-alkylene group to the adjacent group A in each case must take place via the carbonyl group, a —CO—O-alkylene- or —CO—NR$_4$-alkylene group wherein the alkylene moiety in each case contains 1 to 4 carbon atoms, while the linking to the adjacent group A in each case must take place via the carbonyl group, wherein $R_4$ denotes a hydrogen atom or a methyl or ethyl group, or a carbonyl group, C denotes a 2-oxo-morpholin-4-yl group substituted by the group $R_5$ or by the group $R_5$ and a $C_{1-4}$-alkyl group, while $R_5$ denotes a $C_{3-4}$-alkyl, hydroxy-$C_{1-4}$-alkyl, $C_{1-4}$-alkoxy-$C_{1-4}$-alkyl, di-($C_{1-4}$-alkyl)-amino-$C_{1-4}$-alkyl, pyrrolidino-$C_{1-4}$-alkyl, piperidino-$C_{1-4}$-alkyl, morpholino-$C_{1-4}$-alkyl, 4-($C_{1-4}$-alkyl)-piperazino-$C_{1-4}$-alkyl, $C_{1-4}$-alkylsulphanyl-$C_{1-4}$-alkyl, $C_{1-4}$-alkylsulphinyl-$C_{1-4}$-alkyl, $C_{1-4}$-alkylsulphonyl-$C_{1-4}$-alkyl, cyano-$C_{1-4}$-alkyl, $C_{1-4}$-alkoxycarbonyl-$C_{1-4}$-alkyl, aminocarbonyl-$C_{1-4}$-alkyl, $C_{1-4}$-alkyl-aminocarbonyl-$C_{1-4}$-alkyl, di-($C_{1-4}$-alkyl) aminocarbonyl-$C_{1-4}$-alkyl, pyrrolidinocarbonyl-$C_{1-4}$-alkyl, piperidinocarbonyl-$C_{1-4}$-alkyl, morpholinocarbonyl-$C_{1-4}$-alkyl or a 4-($C_{1-4}$-alkyl)-piperazinocarbonyl-$C_{1-4}$-alkyl group, a 2-oxo-morpholin-4-yl group substituted by two groups $R_5$, where $R_5$ is as hereinbefore defined and the two groups $R_5$ may be identical or different, a 2-oxo-morpholin-4-yl group, wherein the two hydrogen atoms of a methylene group are replaced by a —(CH$_2$)$_m$, —CH$_2$—Y—CH$_2$, —CH$_2$—Y—CH$_2$—CH$_2$, —CH$_2$CH$_2$—Y—CH$_2$CH$_2$— or —CH$_2$CH$_2$—Y—CH$_2$CH$_2$CH$_2$— bridge optionally substituted by one or two $C_{1-2}$-alkyl groups, while m denotes the number 2, 3, 4, 5 or 6 and Y denotes an oxygen or sulphur atom, a sulphinyl, sulphonyl or $C_{1-4}$-alkylimino group, a 2-oxo-morpholin-4-yl group, wherein a hydrogen atom in the 5 position together with a hydrogen atom in the 6 position is replaced by a —(CH$_2$)$_n$, —CH$_2$—Y—CH$_2$, —CH$_2$—Y—CH$_2$CH$_2$— or —CH$_2$CH$_2$—Y—CH$_2$-bridge, while Y is as hereinbefore defined and n denotes the number 2, 3 or 4, or, if D together with E denotes a group $R_d$, it may also denote a 2-oxo-morpholin-4-yl group which may be substituted by 1 to 4 $C_{1-2}$-alkyl groups, D denotes a —O—$C_{1-6}$-alkylene group, while the alkylene moiety is linked to the group E, or an oxygen atom, while this may not be linked to a nitrogen atom of the group E, and E denotes an amino group substituted by 2 $C_{1-4}$-alkyl groups, wherein the alkyl groups may be identical or different and each alkyl moiety may be substituted from the 2 position by a $C_{1-4}$-alkoxy or di-($C_{1-4}$-alkyl)-amino group or by a 4- to 7-membered alkyleneimino group, while in the abovementioned 6- to 7-membered alkyleneimino groups in each case a methylene group may be replaced in the 4 position by an oxygen or sulphur atom or by a sulphinyl, sulphonyl- or N—($C_{1-4}$-alkyl)-imino group, a 4- to 7-membered alkyleneimino group optionally substituted by 1 to 4 methyl groups, a 6- to 7-membered alkyleneimino group optionally substituted by 1 or 2 methyl groups, wherein in each case a methylene group in the 4 position is replaced by an oxygen or sulphur atom or by a sulphinyl, sulphonyl- or N—($C_{1-4}$-alkyl)-imino group, an imidazolyl group optionally substituted by 1 to 3 methyl groups, a $C_{5-7}$-cycloalkyl group, wherein a methylene group is replaced by an oxygen or sulphur atom or by a sulphinyl, sulphonyl or N—($C_{1-4}$-alkyl)-imino group, or D together with E denotes a hydrogen atom, a $C_{1-6}$-alkoxy group optionally substituted from the 2 position by a hydroxy- or $C_{1-4}$-alkoxy group, a $C_{3-7}$-cycloalkoxy- or $C_{3-7}$-cycloalkyl-$C_{1-4}$-alkoxy group, or a group $R_d$, where $R_d$ denotes a $C_{2-6}$-alkoxy group which is substituted from the 2 position by a $C_{4-7}$-cycloalkoxy- or $C_{3-7}$-cycloalkyl-$C_{1-3}$-alkoxy group, a $C_{4-7}$-cycloalkoxy- or $C_{3-7}$-cycloalkyl-$C_{1-6}$-alkoxy group wherein the cycloalkyl moiety in each case is substituted by a $C_{1-4}$-alkyl, $C_{1-4}$-alkoxy, di-($C_{1-4}$-alkyl)-amino, pyrrolidino, piperidino, morpholino, piperazino, 4-($C_{1-2}$-alkyl)-piperazino, $C_{1-4}$-alkoxy-$C_{1-2}$-alkyl, di-($C_{1-4}$-alkyl)-amino-$C_{1-2}$-alkyl, pyrrolidino-$C_{1-2}$-alkyl, piperidino-$C_{1-2}$-alkyl, morpholino-$C_{1-2}$-alkyl, piperazino-$C_{1-2}$-alkyl- or 4-($C_{1-2}$-alkyl)-piperazino-$C_{1-2}$-alkyl group, while the abovementioned cycloalkyl moieties may additionally be substituted by a methyl or ethyl group, while, unless otherwise stated, by the aryl moieties mentioned in the definition of the abovementioned groups is meant a phenyl group which may be mono- or disubstituted by $R_6$, while the substituents may be identical or different and $R_6$ denotes a fluorine, chlorine, bromine or iodine atom, a $C_{1-2}$-alkyl, trifluoromethyl or $C_{1-2}$-alkoxy group, or two groups $R_6$, if they are bound to adjacent carbon atoms, together represent a $C_{3-4}$-alkylene, methylenedioxy or 1,3-butadien-1,4-ylene group, or a tautomer or salt thereof.

2. A compound of the formula I according to claim 1, wherein $R_a$ denotes a hydrogen atom, $R_b$ denotes a benzyl or 1-phenylethyl group or a phenyl group substituted by the groups $R_1$ and $R_2$, while $R_1$ denotes a hydrogen, fluorine, chlorine or bromine atom, a methyl, trifluoromethyl, cyano or ethynyl group and $R_2$ denotes a hydrogen or fluorine atom, $R_c$ denotes a hydrogen atom, X denotes a nitrogen atom, A denotes a 1,2-vinylene group, B denotes a $C_{1-4}$-alkylene group, C denotes a 2-oxo-morpholin-4-yl group substituted by the group $R_5$ or by the group $R_5$ and a $C_{1-4}$-alkyl group, while $R_5$ denotes a $C_{3-4}$-alkyl, $C_{1-2}$-alkoxy-$C_{1-4}$-alkyl, di-($C_{12}$-alkyl)-amino-$C_{1-4}$-alkyl, pyrrolidino-$C_{1-4}$-alkyl, piperidino-$C_{1-4}$-alkyl, morpholino-$C_{1-4}$-alkyl, 4-($C_{1-2}$-alkyl)-piperazino-$C_{1-4}$-alkyl, $C_{1-2}$-alkylsulphanyl-$C_{1-4}$-alkyl, $C_{1-2}$-alkylsulphinyl-$C_{1-4}$-alkyl, $C_{1-2}$-alkylsulphonyl-$C_{1-4}$-alkyl, cyano-$C_{1-4}$-alkyl, $C_{1-2}$-alkoxycarbonyl-$C_{1-4}$-alkyl, aminocarbonyl-$C_{1-4}$-alkyl, $C_{1-2}$-alkyl-aminocarbonyl-$C_{1-4}$-alkyl, di-($C_{1-2}$-alkyl)-aminocarbonyl-$C_{1-4}$-alkyl, pyrrolidinocarbonyl-$C_{1-4}$-alkyl, piperidinocarbonyl-$C_{1-4}$-alkyl, morpholinocarbonyl-$C_{1-4}$-alkyl- or a 4-($C_{1-2}$-alkyl)-piperazinocarbonyl-$C_{1-4}$-alkyl group, a 2-oxo-morpholin-4-yl group substituted by two groups $R_5$, while $R_5$ is as hereinbefore defined and the two groups $R_5$ may be identical or different, a 2-oxo-morpholin-4-yl group, wherein the two hydrogen atoms of a methylene group are replaced by a —($CH_2$)$_m$, —$CH_2$—Y—$CH_2$, —$CH_2$—Y—$CH_2$—$CH_2$— or —$CH_2CH_2$—Y—$CH_2CH_2$-bridge, while m denotes the number 2, 3, 4 or 5 and Y denotes an oxygen or sulphur atom, a sulphinyl, sulphonyl or $C_{1-2}$-alkylimino group, a 2-oxo-morpholin-4-yl group, wherein a hydrogen atom in the 5 position together with a hydrogen atom in the 6 position is replaced by a —($CH_2$)$_n$, —$CH_2$—Y—$CH_2$, —$CH_2$—Y—$CH_2CH_2$— or —$CH_2CH_2$—Y—$CH_2$-bridge, where Y is as hereinbefore defined and n denotes the number 2, 3 or 4, or, if D together with E denotes a group $R_d$, it may also denote a 2-oxo-morpholin-4-yl group which may be substituted by 1 or 2 methyl or ethyl groups, D denotes a —O—$C_{1-4}$-alkylene group, while the alkylene moiety is linked to the group E, and E denotes a dimethylamino, diethylamino, pyrrolidino, piperidino, morpholino, 4-methyl-piperazino- or 4-ethyl-piperazino group or D together with E denotes a hydrogen atom, a methoxy, ethoxy, 2-methoxy-ethoxy, 3-methoxy-propyloxy, tetrahydrofuran-3-yloxy, tetrahydropyran-3-yloxy, tetrahydropyran-4-yloxy, tetrahydrofuranylmethoxy or tetrahydropyranylmethoxy group, a cyclobutyloxy, cyclopentyloxy, cyclohexyloxy, cyclopropylmethoxy, cyclobutylmethoxy, cyclopentylmethoxy or cyclohexylmethoxy group or a group $R_d$, where $R_d$ denotes a 2-(cyclobutyloxy)-ethoxy, 2-(cyclopentyloxy)-ethoxy, 2-(cyclopropylmethoxy)-ethoxy or 2-(cyclobutylmethoxy)-ethoxy group, or a tautomer or salt thereof.

3. A compound of the formula I according to claim 1, wherein $R_a$ denotes a hydrogen atom, $R_b$ denotes a 1-phenylethyl, 3-methylphenyl, 3-chlorophenyl, 3-bromophenyl- or 3-chloro-4-fluorophenyl group, $R_c$ denotes a hydrogen atom, X denotes a nitrogen atom, A denotes a 1,2-vinylene group, B denotes a methylene group, C denotes a 2-oxo-morpholin-4-yl group which is substituted by a methoxymethyl, methoxyethyl, ethoxymethyl, ethoxyethyl, dimethylaminomethyl, dimethylaminoethyl, diethylaminomethyl, diethylaminoethyl, cyanomethyl or cyanoethyl group, a 2-oxo-morpholin-4-yl group, wherein the two hydrogen atoms of a methylene group are replaced by a —$CH_2CH_2$—, —$CH_2CH_2CH_2$—, —$CH_2CH_2CH_2CH_2$—, —$CH_2CH_2CH_2CH_2CH_2$—, —$CH_2$—O—$CH_2CH_2$—, —$CH_2$—$NCH_3$—$CH_2CH_2$—, —$CH_2$—$NC_2H_5$—$CH_2CH_2$—, —$CH_2CH_2$—O—$CH_2CH_2$—, —$CH_2CH_2$—$NCH_3$—$CH_2CH_2$— or —$CH_2CH_2$—$NC_2H_5$—$CH_2CH_2$— bridge, a 2-oxo-morpholin-4-yl group, wherein a hydrogen atom in the 5 position together with a hydrogen atom in the 6 position is replaced by a —$CH_2CH_2CH_2$—, —$CH_2CH_2CH_2CH_2$—, —$CH_2$—O—$CH_2$—, —$CH_2$—$NCH_3$—$CH_2$—, —$CH_2$—$NC_2H_5$—$CH_2$—, —$CH_2$—O—$CH_2CH_2$—, —$CH_2$—$NCH_3$—$CH_2CH_2$—, —$CH_2$—$NC_2H_5$—$CH_2CH_2$—, —$CH_2CH_2$—O—$CH_2$—, —$CH_2CH_2$—$NCH_3$—$CH_2$— or —$CH_2CH_2$—$NC_2H_5$—$CH_2$— bridge, or, if D together with E denotes a group $R_d$, it may also denote a 2-oxo-morpholin-4-yl group which is substituted by 1 or 2 methyl groups, and D together with E denotes a hydrogen atom, a methoxy, ethoxy, 2-methoxy-ethoxy, 3-methoxy-propyloxy, tetrahydrofuran-3-yloxy, tetrahydropyran-4-yloxy or tetrahydrofuranylmethoxy group, a cyclobutyloxy, cyclopentyloxy, cyclopropylmethoxy, cyclobutylmethoxy or cyclopentylmethoxy group or a group $R_d$, where $R_d$ denotes a 2-(cyclobutyloxy)-ethoxy, 2-(cyclopentyloxy)-ethoxy, 2-(cyclopropylmethoxy)-ethoxy or 2-(cyclobutylmethoxy)-ethoxy group, or a tautomer or salt thereof.

4. A compound of the formula I according to claim 1, wherein $R_a$ denotes a hydrogen atom, $R_b$ denotes a 3-chloro-4-fluorophenyl group, $R_c$ denotes a hydrogen atom, X denotes a nitrogen atom, A denotes a 1,2-vinylene group, B denotes a methylene group, C denotes a 2-oxo-morpholin-4-yl group which is substituted by a methoxymethyl or methoxyethyl group, or a 2-oxo-morpholin-4-yl group, wherein the two hydrogen atoms of a methylene group are replaced by a —$CH_2CH_2$—O—$CH_2CH_2$— bridge, and D together with E denotes a hydrogen atom, a methoxy or cyclopropylmethoxy group, or a tautomer or salt thereof.

5. A compound selected from the group consisting of:

(1) 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, (2) 4-[(3-chloro-4-fluoro-phenyl)amino]-6-{[4-(2-oxo-1,9-dioxa-4-aza-spiro[5,5]undec-4-yl)-1-oxo-2-buten-1-yl]amino}-7-cyclopropylmethoxy-quinazoline and (3) 4-[(3-chloro-4-fluoro-phenyl)amino]-6-({4-[2-(2-methoxy-ethyl)-6-oxo-morpholin-4-yl]-1-oxo-2-buten-1-yl}amino)-7-cyclopropylmethoxy-quinazoline,
or a tautomer or salt thereof.

6. A physiologically acceptable salt of a compound according to claim 1, 2, 3, 4 or 5, formed with an inorganic or organic acid or base.

7. A pharmaceutical composition comprising a compound according to claim 1, 2, 3, 4 or 5 or a pharmaceutically acceptable salt thereof and a pharmaceutically acceptable carrier or diluent.

8. A method of treating a malignant tumour or a disease of the respiratory tract or lungs which is accompanied by increased or altered production of mucus caused by stimulation of tyrosine kinases, which comprises administering a therapeutically effective amount of a compound according claim 1, 2, 3, 4 or 5 or a pharmaceutically acceptable salt thereof.

* * * * *